United States Patent
Tsujita et al.

(10) Patent No.: US 6,694,176 B1
(45) Date of Patent: Feb. 17, 2004

(54) METHOD AND APPARATUS FOR DETECTING FLUORESCENCE USED FOR DETERMINING CONDITIONS OF TISSUE

(75) Inventors: Kazuhiro Tsujita, Kaisei-machi (JP); Katsumi Hayashi, Kaisei-machi (JP)

(73) Assignee: Fuji Photo Film Co., Ltd., Kanagawa-ken (JP)

(*) Notice: Subject to any disclaimer, the term of this patent is extended or adjusted under 35 U.S.C. 154(b) by 215 days.

(21) Appl. No.: 09/672,766

(22) Filed: Sep. 29, 2000

(30) Foreign Application Priority Data

Sep. 30, 1999 (JP) .......................................... 11-279687

(51) Int. Cl.[7] .............................................. A61B 6/00
(52) U.S. Cl. ........................................ 600/477; 600/478
(58) Field of Search ................................ 600/476, 477, 600/488, 182, 478; 356/303, 318; 250/458.1; 436/63, 171, 172

(56) References Cited

U.S. PATENT DOCUMENTS 5,421,337 A * 6/1995 Richards-Kortum et al. ..... 600/477
6,070,096 A * 5/2000 Hayashi ....................... 600/477

* cited by examiner

Primary Examiner—Ruth S. Smith
(74) Attorney, Agent, or Firm—Sughrue, Mion, PLLC

(57) ABSTRACT

A method and an apparatus for detecting fluorescence to distinguish between a sub mucosa and a mucosa immediately and easily. The sub mucosa of organic tissue is distinguished from and the mucosa thereof based on autofluorescence emitted from the organic tissue in response to stimulating light projected thereon. The distinction between the sub mucosa and the mucosa is made based on normalized intensity of the autofluorescence emitted from the organic tissue utilizing the fact that the spectrum of autofluorescence emitted from the sub mucosa is different from the spectrum of autofluorescence emitted from the mucosa.

17 Claims, 4 Drawing Sheets

METHOD AND APPARATUS FOR DETECTING FLUORESCENCE USED FOR DETERMINING CONDITIONS OF TISSUE

BACKGROUND OF THE INVENTION

1. Field of the Invention

The present invention relates to a method and an apparatus for detecting fluorescence for determining conditions of organic tissue based on autofluorescence emitted therefrom in response to stimulating light projected thereon, and more particularly, to a method and an apparatus for distinguishing between the mucosa and the sub mucosa by detecting fluorescence emitted from the organic tissue.

2. Description of the Related Art

Endoscopic mucosal resection (hereinafter, called EMR) has been widely used as a remedy for cancer in which a lesion on a mucosa affected with cancer in early stages is extirpated while being observed with an endoscope. EMR is an effective remedy which is less invasive than surgical remedies. EMR is directed at cancer in its early stages which has affected a mucosa of organic tissue but has not yet affected a sub mucosa thereunder. The mucosa affected with cancer in its early stages is extirpated using a treating instrument for resection guided thereto by the endoscope.

However, even if an affected area on the mucosa is extirpated through the EMR treatment, it may sometimes result in incomplete removal of the mucosa and an unremoved lesion affected with cancer (hereinafter, called residual) may still reside on a fraction of the mucosa remaining on the treated area. An incidence of the residual is low in the case where the affected area is small and the entire lesion on the mucosa can be extirpated with a single resection process. However, in the case where the affected area is large and a plurality of resection processes must be performed, the incidence of the residual becomes higher as the number of the resection processes increases. Whether or not the mucosa is remaining on the treated area after the EMR treatment is judged by examining a condition of the organic tissue sampled from the treated area. Such examination takes a considerable time and requires additional endoscopic treatment. Therefore, though EMR is a non-invasive and effective remedy, it has a disadvantage of making it difficult to check if the treatment was completely done immediately after the treatment.

SUMMARY OF THE INVENTION

The objective of the present invention is to provide a method and an apparatus for detecting fluorescence to distinguish between a sub mucosa and a mucosa immediately and easily.

In the first method of the present invention, a sub mucosa of organic tissue is distinguished from a mucosa thereof based on autofluorescence emitted from the organic tissue in response to stimulating light projected thereon, wherein the sub mucosa is distinguished from the mucosa based on the normalized intensity of the autofluorescence emitted from the organic tissue utilizing the fact that the spectrum of autofluorescence emitted from the sub mucosa is different from the spectrum of autofluorescence emitted from the mucosa.

In the second method of the present invention, judgment is made on whether or not a sub mucosa and a mucosa coexist on the area under examination based on autofluorescence emitted from organic tissue within the area under examination in response to stimulating light projected thereon, wherein the judgment is made by comparing the normalized intensity of the autofluorescence emitted from the organic tissue with a standard value which is decided based on the normalized intensity of autofluorescence emitted from the sub mucosa and/or the normalized intensity of autofluorescence emitted from the mucosa.

In the third method of the present invention, judgment is made on whether the organic tissue under examination is of a sub mucosa or a mucosa based on autofluorescence emitted from the organic tissue in response to stimulating light projected thereon, wherein the judgment is made by comparing the normalized intensity of the autofluorescence emitted from the organic tissue with a standard value which is decided based on the normalized intensity of autofluorescence emitted from the sub mucosa and/or the normalized intensity of autofluorescence emitted from the mucosa.

The first apparatus of the present invention comprises distinguishing means for distinguishing a sub mucosa of organic tissue from a mucosa thereof based on autofluorescence emitted from the organic tissue in response to stimulating light projected thereon, wherein the distinguishing means distinguishes the sub mucosa from the mucosa based on the normalized intensity of the autofluorescence emitted from the organic tissue utilizing the fact that the spectrum of autofluorescence emitted from the sub mucosa is different from the spectrum of autofluorescence emitted from the mucosa.

The second apparatus of the present invention comprises distinguishing means for making judgment on whether or not a sub mucosa and a mucosa coexist on the area under examination based on autofluorescence emitted from organic tissue within the area under examination in response to stimulating light projected thereon, wherein the distinguishing means makes judgment by comparing the normalized intensity of the autofluorescence emitted from the organic tissue with a standard value which is decided based on the normalized intensity of autofluorescence emitted from the sub mucosa and/or the normalized intensity of autofluorescence emitted from the mucosa.

The third apparatus of the present invention comprises distinguishing means for making judgment on whether the organic tissue under examination is of a sub mucosa or a mucosa based on autofluorescence emitted from the organic tissue in response to stimulating light projected thereon, wherein the distinguishing means makes judgment by comparing the normalized intensity of the autofluorescence emitted from the organic tissue with a standard value which is decided based on the normalized intensity of autofluorescence emitted from the sub mucosa and/or the normalized intensity of autofluorescence emitted from the mucosa.

Each of the normalized intensities to be used with the methods and apparatuses described above is preferably the normalized band intensity for a wavelength region near 480 nm.

Each of the above apparatuses for detecting fluorescence may additionally comprise optical fiber means for transferring the autofluorescence emitted from the organic tissue which is incident on one end thereof to the distinguishing means, wherein the optical fiber means may be run through a tube path extending between a handling portion and the operating end of an endoscope.

The tube path through which the optical fiber means is run may be led through an inner area of a treating instrument of the endoscope.

The inventors of the present invention noticed in the course of the studies on techniques for detecting fluorescence that it is possible to distinguish the sub mucosa from the mucosa utilizing the fact that the fluorescence emitted from the sub mucosa and the fluorescence emitted from the mucosa present different distributions of the spectral intensity even if induced by the same stimulating light. The present invention is based on such findings.

According to the methods and the apparatuses of the present invention for detecting fluorescence, it is possible to distinguish the sub mucosa from the mucosa based on the normalized intensity of the autofluorescence emitted from the organic tissue in response to stimulating light projected thereon utilizing the fact that the spectrum of the autofluorescence emitted from the sub mucosa is different from the spectrum of the autofluorescence emitted from the mucosa (the first method and apparatus for detecting fluorescence), to judge whether or not the sub mucosa and the mucosa coexist on the treated area by comparing the normalized intensity of the autofluorescence emitted from the organic tissue with the standard value which is decided based on the normalized intensity of autofluorescence emitted from the sub mucosa and/or the normalized intensity of autofluorescence emitted from the mucosa (the second method and apparatus for detecting fluorescence), or to distinguish the sub mucosa from the mucosa by comparing the normalized intensity of the autofluorescence emitted from the organic tissue with the standard value which is decided based on the normalized intensity of autofluorescence emitted from the sub mucosa and/or the normalized intensity of autofluorescence emitted from the mucosa (the third method and apparatus for detecting fluorescence). With each method or apparatus, the sub mucosa can easily be distinguished from the mucosa based on the normalized intensity of the autofluorescence. The present invention therefore enables us to check whether the EMR treatment was completely done immediately after the treatment by examining whether the entire mucosa on the treated area has been completely removed revealing the sub mucosa thereunder, instead of, for example, requiring us to sample the organic tissue from the treated area and examine whether or not the diseased tissue is remaining thereon by way of time-consuming tissue inspection carried out after the EMR treatment. Thus, the time required for the check can be remarkably shortened. If the mucosa still remained on the treated area partially, the EMR treatment could be repeated until the entire mucosa would be removed from the area.

Accuracy of the above distinction can be further improved by using the normalized band intensity taken for a wavelength region near 480 nm.

In addition, the distinction can be practiced more easily by providing the apparatus for detecting fluorescence with the optical fiber means for transferring the autofluorescence incident on one end thereof to the distinguishing means and running the optical fiber means through the tube path connecting the handling portion and the operating end of the endoscope. The tube path through which the optical fiber means is run may be led through the inner area of the treating instrument of the endoscope.

DESCRIPTION OF THE PREFERRED EMBODIMENTS

The structure of the endoscope apparatus according to one embodiment of the present invention will now be described with reference to FIGS. 1 and 2 of the accompanying drawings.

Figure 1:
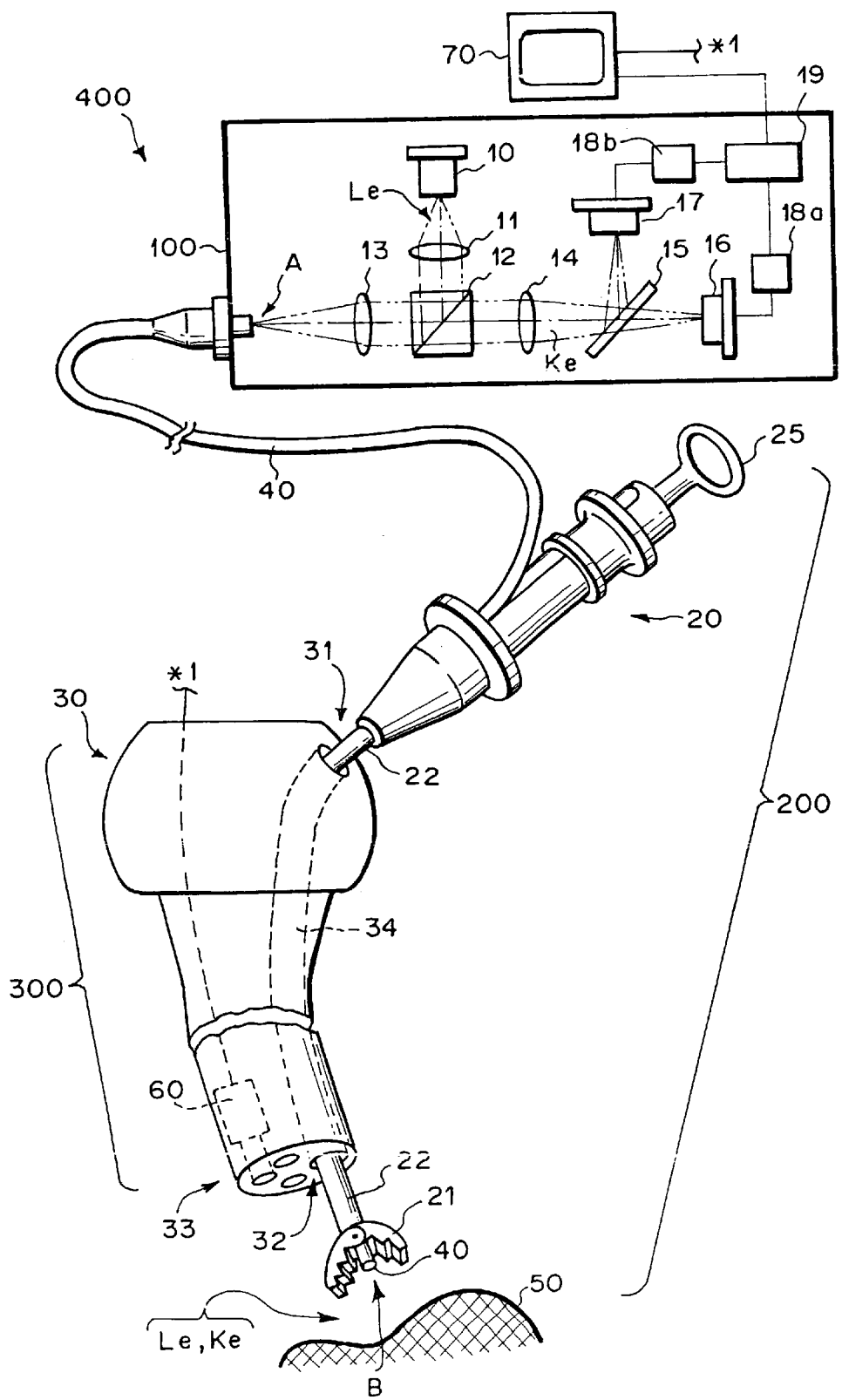
FIG. 1 is a schematic diagram showing the structure of the endoscope apparatus according to one embodiment of the present invention.

Referring to FIG. 1, the endoscope apparatus 400 according to the present invention is constituted of a fluorescence measuring unit 100 which emits stimulating light Le as pulses at the wavelength of 410 nm and which receives as an input autofluorescence Ke induced on organic tissue 50 irradiated with the stimulating light Le, a cable-like optical fiber probe 40 which leads the stimulating light Le emitted from the fluorescence measuring unit 100 to the vicinity of the organic tissue 50 to irradiate the organic tissue 50 with the stimulating light Le and which leads the autofluorescence Ke induced on the organic tissue 50 back to the fluorescence measuring unit 100, a forceps unit 200 provided with a tube path through which the cable-like optical fiber probe 40 is run, and an endoscope 300 which leads an operating end of the forceps unit 200 to the vicinity of the organic tissue 50.

The fluorescence measuring unit 100 contains two sets of optical paths therein, one for emitting the stimulating light Le and the other for measuring the autofluorescence Ke. The stimulating light Le emitted from a solid laser 10 is collimated by a collimator lens 11, is reflected by a dichroic beam splitter 12 in the direction which is substantially perpendicular to the original optical path of the stimulating light Le, is focused by a collective lens 13, enters the optical fiber probe 40 from the end face A thereof which is fixed on a side wall of the fluorescence measuring unit 100, is transferred via the optical fiber probe 40, and then comes out of the optical fiber probe 40 at the end face B.

On the other hand, the autofluorescence Ke having wavelengths longer than the wavelength of the stimulating light Le is induced on the organic tissue 50 in response to the stimulating light Le projected thereon, enters the optical fiber probe 40 from the end face B, is transferred via the optical fiber probe 40, comes out of the optical fiber probe 40 at the end face A, is collimated by the collective lens 13, passes the dichroic beam splitter 12, is focused by a fluorescence collective lens 14, and then is divided by a dichroic mirror 15 located on the converging path so that a portion of the fluorescence Ke within a middle wavelength region follows one optical path leading to a photodiode 16 for the middle wavelengths and the remaining portions of the fluorescence Ke corresponding to those wavelengths out of the middle wavelength region (i.e. the portions within end wavelength regions) follows the other optical path leading to a photodiode 17 for the end wavelengths.

The optical path which leads the stimulating light Le from the fluorescence measuring unit 100 to the operating end 33 of the endoscope and the optical path which leads the autofluorescence Ke from the operating end 33 back to the fluorescence measuring unit 100 actually share a single physical path realized by the optical fiber probe 40.

The dichroic beam splitter 12 is designed to reflect the light having a wavelength of 410 nm or shorter and transmit the light having a wavelength longer than 410 nm, and therefore reflects the stimulating light Le and transmits the autofluorescence Ke. The dichroic mirror 15 is designed to transmit the light having a wavelength within the middle wavelength region, namely within the region of 480 nm±20 nm, and reflect the light having a wavelength out of the middle wavelength region, namely within the end wavelength regions covering those wavelengths shorter than 460 nm or longer than 500 nm.

A forceps tube 22 is connected to a tip 30 of a handling portion 20 of the forceps unit 200 at one end and is provided with gripping forceps 21 at the other end. The gripping forceps 21 for gripping and lifting the organic tissue 50 is connected with a linked lever 25 of the handling portion 20 by way of a wire run through the forceps tube 22 so that the gripping forceps 21 may open and close following operation at the linked lever 25. The end face B of the optical fiber probe 40 is inserted into the forceps tube 22 at one end via the handling portion 20 and then is projected from the center of the gripping forceps 21 fixed on the other end of the forceps tube 22.

The gripping forceps 21 keep the operating end 33 of the endoscope at an appropriate position with respect to the organic tissue 50 by gripping the organic tissue 50 and thus help fix the operating end 33 at an appropriate position with respect to the area to be treated when conducting the EMR treatment.

The endoscope 300 is provided with a forceps tube path 34 for leading the forceps tube 22 from the tip 30 of the handling portion 20 to the operating end 33 of the endoscope, wherein ends of the forceps tube path 34 are hereinafter referred to as a forceps entrance 31 and a forceps exit 32, respectively. The forceps tube 22 is inserted into the forceps tube path 34 at the forceps entrance 31, run through the forceps tube path 34, projected out of the forceps tube path 34 at the forceps exit 32, and led to the vicinity of the organic tissue 50 which is to be examined. The forceps tube 22 can be freely inserted into and removed out of the forceps tube path 34 of the endoscope 300 and the treating instrument employing the gripping forceps 21 can be replaced by treating instruments of other types.

Figure 2:
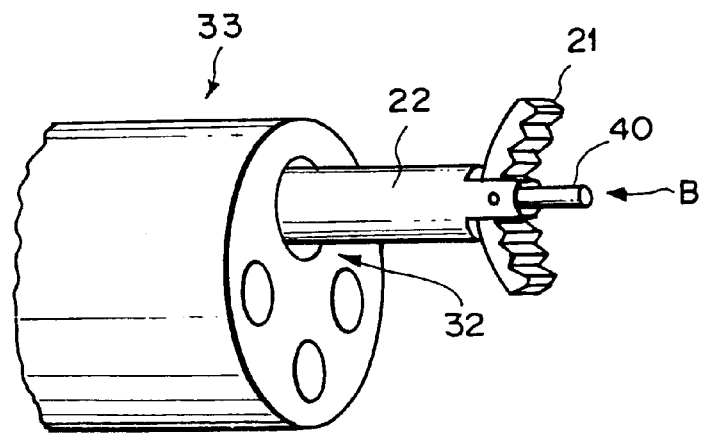
FIG. 2 shows an operating end of the endoscope including a forceps tube path, a forceps tube and an optical fiber probe.

As is shown in FIG. 2 which is an enlarged view of the operating end 33 of the endoscope 300, the optical fiber probe 40 is inserted into the forceps tube 22, which is further inserted into the forceps tube path 32 of the endoscope 300.

Also shown in FIG. 2 are several other tube paths reserved for other units used in the EMR treatment. Also incorporated in the operating end 33 of the endoscope 300 is a normal imaging unit 60 (see FIG. 1) constituted of a light source which emits white light as pulses to help observation of the organic tissue, an imaging optical system, an imaging element, etc. A television monitor 70 displays those normal images taken by the normal imaging unit 60. The pulse-like white light illuminates the organic tissue 50 when the pulse-like stimulating light does not, and vice versa, and the normal imaging unit 60 takes the image of the organic tissue 50 only when the pulse-like white light is illuminating the organic tissue 50. Thus, an image taken by the normal imaging unit 60 always shows the organic tissue 50 illuminated with the white light.

How the apparatus of the above embodiment operates will now be explained in the following. It is assumed herein that the EMR treatment has already been administered to the area affected with cancer in early stages using treating instruments inserted into the tube paths for those instruments and the substantial portion of the mucosa has already been extirpated therefrom, and that the operating end 33 of the endoscope is now located in the vicinity of the treated area.

At this stage, the forceps tube 22 of the forceps unit 200 containing the optical fiber probe 40 inserted therein is inserted into the forceps tube path 34 at the forceps entrance 31, run through the forceps tube path 34, and projected out of the forceps tube path 34 at the forceps exit 32.

The first step for distinguishing the sub mucosa from the mucosa is to locate the end face B of the optical fiber probe 40 at an appropriate position and then irradiate the treated area with the stimulating light Le, which is emitted by the solid laser 10 and led to the end face B, while observing on the television monitor 70 the images of the treated area taken by the normal imaging unit 60. The treated area irradiated with the stimulating light Le emits the autofluorescence Ke. The autofluorescence Ke then enters the optical fiber probe 40 from the end face B, comes out of the optical fiber probe 40 at the end face A, passes the collective lens 13, the dichroic beam splitter 12 and the fluorescence collective lens 14, and is divided by the dichroic mirror 15 located on the converging path into the portion of the fluorescence Ke within the middle wavelength region and the remaining portions of the fluorescence Ke within the end wavelength regions. The former portion is received by the photodiode 16 for the middle wavelengths and the latter portions are received by the photodiode 17 for the end wavelengths. The detected intensity of the former portion and the detected intensity of the latter portions are converted to electrical signals, and then to numerical values, namely data Dc representing the intensity of the fluorescence in the middle wavelength region and data Dr representing the intensity of the fluorescence in the end wavelength regions, by an A/D converter 18a and an A/D converter 18b, respectively. The data Dc and Dr are then received by a distinguishing device 19 and the normalized intensity Kk is derived therein for the fluorescence in the middle wavelength region using the equation $Kk=Dc/(Dc+Dr)$. The distinguishing device 19 determines where the autofluorescence Ke originates (the mucosa or the sub mucosa) by comparing the value of the normalized intensity Kk with a threshold value Q, a standard value stored in the distinguishing device 19 for distinguishing the sub mucosa from the mucosa. The threshold value Q is the standard value calculated in advance by taking the middle value between the normalized intensity derived using the above method for an area on the organic tissue already judged to be a portion of the sub mucosa according to a method different from the above one and the normalized intensity derived using the above method for an area on the organic tissue already judged to be a portion of the mucosa according to the method different from the above one.

The distinguishing device 19 outputs the result of the judgement based on the threshold value Q and the result is displayed on the television monitor 70 along with the image of the treated area taken by the normal imaging unit 60.

As the result of the judgement can be obtained immediately, it is possible to check immediately after the EMR treatment whether the entire mucosa has been completely removed from the treated area revealing the sub mucosa thereunder by applying the above distinguishing operation throughout the treated area while observing the normal image of the treated area on the television monitor 70.

Figure 3:
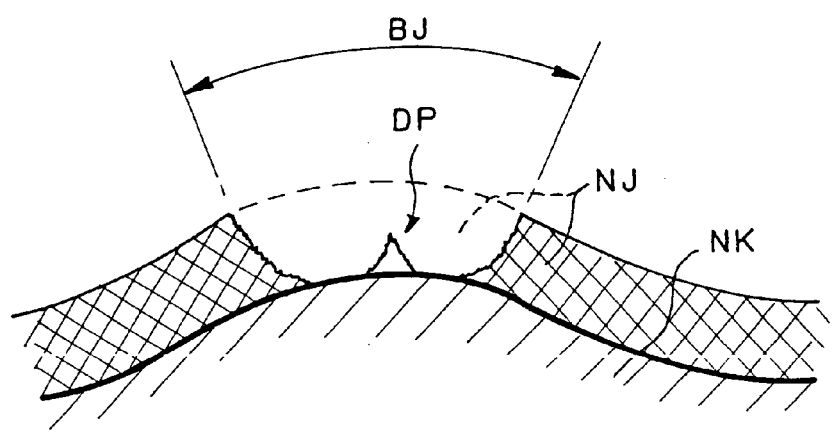
FIG. 3 is a schematic diagram showing a treated area.
Figure 4:
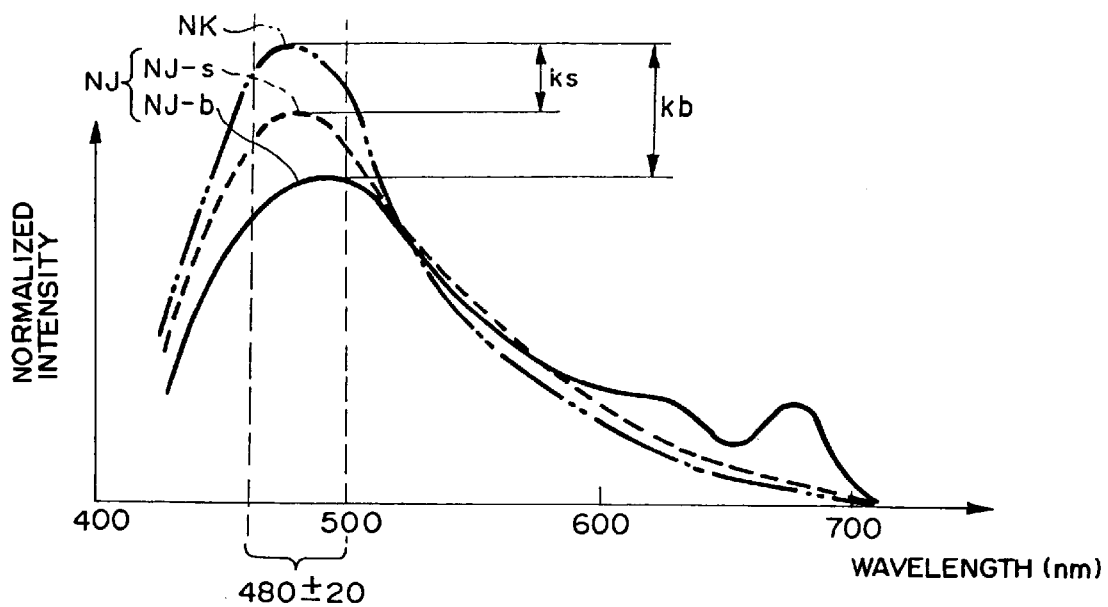
FIG. 4 is a graph showing the normalized intensities of autofluorescence emitted from three types of organic tissue in different conditions.

Now, the operation of distinguishing the sub mucosa from the mucosa will be explained in detail. FIG. 3 is a cross-sectional view of a treated area after the EMR treatment. Although the mucosa NJ has been removed from most parts of the treated area BJ revealing the sub mucosa NK thereunder, a fraction Dp of the mucosa NJ is occasionally remaining on the treated area BJ. The fraction Dp is sometimes normal tissue and at other times diseased tissue. Thus, the autofluorescence emitted from the treated area BJ in response to the stimulating light Le may be composed of three different kinds of autofluorescence each emitted from the tissue of the sub mucosa NK, the normal tissue of the mucosa NJ or the diseased tissue of the mucosa NJ. These three kinds of tissue cannot be distinguished from one another based solely on the intensities of the autofluorescence emitted therefrom as the intensities of the autofluorescence may vary significantly according to measuring conditions (e.g. the distance or the angle between the tissue and the end face B of the optical fiber probe 40). However, as shown in FIG. 4, the three kinds of autofluorescence present different distribution profiles of the spectral intensity, each having characteristic features which may hardly be influenced by the measuring conditions, when each of the distributions is normalized with the total intensity integrated over all wavelengths. Especially in the wavelength region of 480 nm±20 nm, the differences between the normalized intensities of the autofluorescence emitted from the three kinds of tissue are remarkable and the three kinds of tissue can be ordered in accordance with the normalized intensity thereof, i.e. the tissue of the sub mucosa NK, the normal tissue of the mucosa NJ-s and then the diseased tissue of the mucosa NJ-b in the order of the normalized intensity. Accordingly, it is possible to judge whether or not the entire mucosa NJ has been removed from the treated area BJ by comparing the measured normalized intensity of the autofluorescence with the threshold value Q.

The value of the total spectral intensity of the autofluorescence integrated over all wavelengths is represented by the value of (Dc+Dr), and the value of the spectral band intensity of the autofluorescence integrated over the wavelength region of 480 nm±20 nm is represented by the value of Dc.

EMR is the remedy in which the mucosa NJ is removed from every part of the treated area BJ and the judgment of whether or not the EMR treatment has been completely done is made by determining whether or not the mucosa NJ still resides in the treated area BJ. To be exact, what is important for avoiding occurrence of the residual is to judge whether or not the diseased tissue of the mucosa NJ-b still resides in the treated area BJ. However, the present distinguishing procedure is rather effective in avoiding occurrence of the residual, because the possibility of erroneously determining the diseased tissue of the mucosa NJ-b as the tissue of the sub mucosa NK is much lower than the possibility of erroneously determining the normal tissue of the mucosa NJ-s as the tissue of the sub mucosa NK as the difference kb between the normalized intensity of the tissue of the sub mucosa NK and that of the diseased tissue of the mucosa NJ-b is larger than the difference ks between the tissue of the sub mucosa NK and the normal tissue of the mucosa NJ-s as shown in FIG. 4.

The distinguishing procedure is carried out throughout the entire surface of the treated area BJ and additional EMR treatment is performed for those spots determined as fractions of the mucosa NJ. The EMR treatment and the operation of distinguishing the sub mucosa NK from the mucosa NJ are terminated when the treated area BJ is judged to have no residual portion of the mucosa NJ.

The distinguishing techniques of the present invention should not be limited to the above-described techniques of comparing the normalized intensities each derived by dividing the band intensity of the autofluorescence taken for the wavelength region of 480 nm±20 nm by the total intensity integrated over all wavelengths. Instead, a wavelength region of any central wavelength and any width can be adopted as far as the sub mucosa and the mucosa present the normalized intensities remarkably different from each other in the wavelength region. In addition, the measured intensity can be divided by a value other than the total intensity integrated over all wavelengths to obtain the normalized intensity. For example, the measured intensity can be divided by the remainder of the total intensity integrated over all wavelengths from which the band intensity integrated over the wavelength region of 480 nm±20 nm is subtracted.

Furthermore, the threshold value Q used for distinguishing the sub mucosa from the mucosa may also be replaced by a standard value of another type. For example, it is allowable to adopt as the standard value the normalized band intensity derived for the middle wavelength region for the autofluorescence emitted from the tissue of the mucosa which is known to be the normal tissue and determine the tissue which emits the autofluorescence having the normalized band intensity of 120% of the standard value or more in the middle wavelength region as the tissue of the sub mucosa.

A standard value of any other type may be adopted as far as it works as an appropriate standard for distinguishing the sub mucosa from the mucosa.

Figure 5:
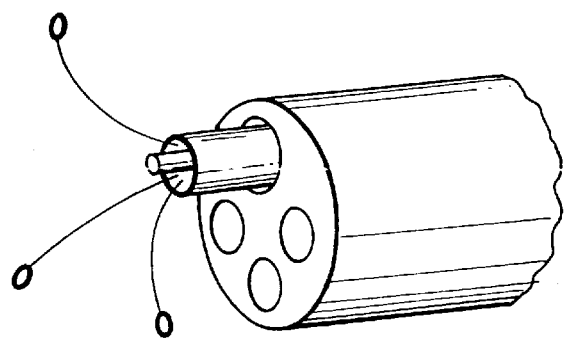
FIG. 5 shows another example of the gripping forceps which works in combination with the optical fiber probe.
Figure 6:
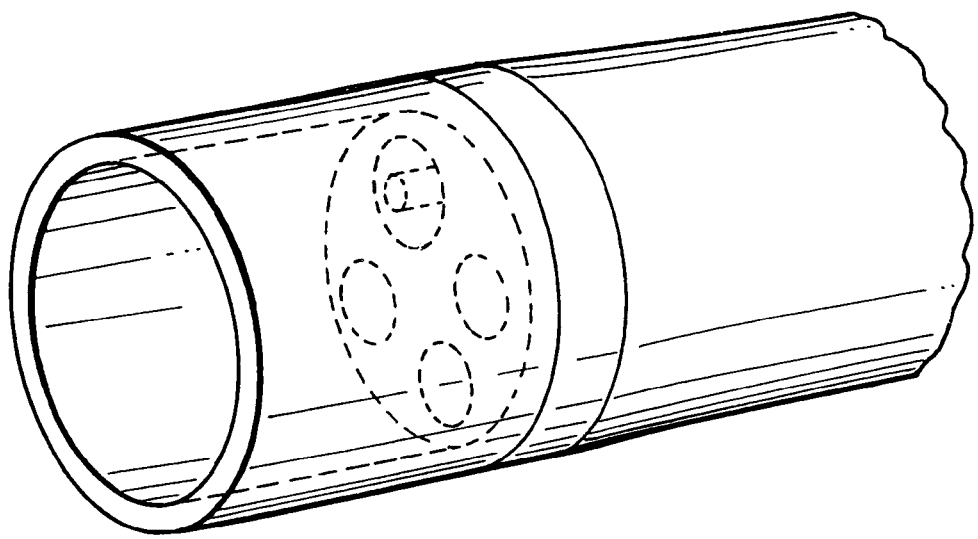
FIG. 6 shows an operating end of the endoscope provided with a spacer.

The optical fiber probe 40 is not required to be constructed in combination with the forceps unit 200 and may instead be constructed in combination with a treatment unit of another kind. For example, the operating end of the optical fiber probe 40 may be combined with a treatment unit such as tripod-type gripping forceps provided with three legs for catching the area to be measured on the organic tissue as shown in FIG. 5, or with a spacer for keeping the area to be measured at a predetermined distance as shown in FIG. 6.

The distinguishing techniques of the present invention may also be applied to diagnosis of an ulcer etc., the diseases in which the mucosa peels off from the affected area.

In summary, the method and the apparatus for detecting fluorescence according to the present invention can be used to distinguish the sub mucosa from the mucosa immediately and easily. The present invention therefore makes it possible to check if the EMR treatment was completely done immediately after the treatment and reduces both burdens on patients and the incidence of the residual.

In addition, all of the contents of Japanese Patent Application No. 11(1999)-279687 are incorporated into this specification by reference.

What is claimed is:

1. A method for detecting fluorescence in which a sub mucosa of organic tissue is distinguished from a mucosa thereof comprising:

projecting a stimulating light onto the organic tissue;

distinguishing the mucosa from the sub mucosa based on a normalized intensity of an autofluorescence emitted from the organic tissue utilizing the fact that the spectrum of autofluorescence emitted from the sub mucosa is different from the spectrum of autofluorescence emitted from the mucosa, wherein the autofluorescence emitted from the organic tissue has an overall integrated intensity, said method further comprising filtering the autofluorescence emitted from the organic tissue to isolate a first wavelength region, and wherein the normalized intensity comprises the intensity of the autofluorescence in the first wavelength region, divided by the intensity over the overall integrated intensity.

2. The method of claim 1, wherein the method distinguishes mucosa and sub-mucosa in an in vivo environment.

3. The method of claim 1, wherein the first wavelength region includes a wavelength range of 460–500 nm.

4. A method for detecting fluorescence comprising: determining whether an organic tissue under examination is of a sub mucosa or a mucosa based on autofluorescence emitted from the organic tissue in response to stimulating light projected thereon, by comparing a normalized intensity of the autofluorescence emitted from the organic tissue with a standard value which is decided based on at least one of: the normalized intensity of autofluorescence emitted from the sub mucosa and the normalized intensity of autofluorescence emitted from the mucosa, wherein the autofluorescence emitted from the organic tissue has an overall integrated intensity, said method further comprising filtering the autofluorescence emitted from the organic tissue to isolate a first wavelength region, and wherein the normalized intensity comprises the intensity of the autofluorescence in the first wavelength region, divided by the intensity over the overall integrated intensity.

5. A method for detecting fluorescence comprising: determining whether or not a sub mucosa and a mucosa coexist on an area under examination based on autofluorescence emitted from an organic tissue within the area under examination in response to stimulating light projected thereon, by comparing a normalized intensity of the autofluorescence emitted from the organic tissue with a standard value which is decided based on at least one of: the normalized intensity of autofluorescence emitted from the sub mucosa and the normalized intensity of autofluorescence emitted from the mucosa, wherein the autofluorescence emitted from the organic tissue has an overall integrated intensity, said method further comprising filtering the autofluorescence emitted from the organic tissue to isolate a first wavelength region, and wherein the normalized intensity comprises the intensity of the autofluorescence in the first wavelength region, divided by the intensity over the overall integrated intensity.

6. An apparatus for detecting fluorescence comprising:

an optical system guiding light emitted from an organic tissue; and distinguishing means receiving light output by the optical system for distinguishing a sub mucosa of organic tissue from a mucosa thereof based on autofluorescence emitted from the organic tissue in response to stimulating light projected thereon, wherein the distinguishing means distinguishes the sub mucosa from the mucosa based on the normalized intensity of the autofluorescence emitted from the organic tissue utilizing the fact that the spectrum of autofluorescence emitted from the sub mucosa is different from the spectrum of the autofluorescence emitted from the mucosa, wherein the autofluorescence emitted from the organic tissue has an overall integrated intensity, said apparatus further comprising means for filtering the autofluorescence emitted from the organic tissue to isolate a first wavelength region, and wherein the normalized intensity comprises the intensity of the autofluorescence in the first wavelength region, divided by the intensity over the overall integrated intensity.

7. An apparatus for detecting fluorescence according to claim 6, said apparatus being operable with an endoscope further comprising:

an optical fiber for transferring the autofluorescence emitted from the organic tissue which is incident on one end thereof to the distinguishing means, wherein the optical fiber is run through a tube path extending between a handling portion and the operating end of the endoscope.

8. An apparatus for detecting fluorescence according to claim 7, wherein the tube path through which the optical fiber is run is led through an inner area of a treating instrument of the endoscope.

9. The apparatus of claim 6, further comprising a stimulating light source providing the stimulating light, wherein the stimulating light source outputs a constant stimulating light for the mucosa and sub mucosa.

10. An apparatus for detecting fluorescence comprising:

an optical system guiding light emitted from an organic tissue; and distinguishing means receiving a light output from the optical system, said distinguishing means for making judgment on whether the organic tissue under examination is of a sub mucosa or a mucosa based on autofluorescence emitted from the organic tissue in response to stimulating light projected thereon, wherein the distinguishing means makes judgment by comparing the normalized intensity of the autofluorescence emitted from the organic tissue with a standard value which is decided based on at least one of the normalized intensity of autofluorescence emitted from the sub mucosa and the normalized intensity of autofluorescence emitted from the mucosa, wherein the autofluorescence emitted from the organic tissue has an overall integrated intensity, said apparatus further comprising means for filtering the autofluorescence emitted from the organic tissue to isolate a first wavelength region, and wherein the normalized intensity comprises the intensity of the autofluorescence in the first wavelength region, divided by the intensity over the overall integrated intensity.

11. An apparatus for detecting fluorescence according to claim 10, said apparatus being operable with an endoscope further comprising:

an optical fiber for transferring the autofluorescence emitted from the organic tissue which is incident on one end thereof to the distinguishing means, wherein the optical fiber is run through a tube path extending between a handling portion and the operating end of the endoscope.

12. An apparatus for detecting fluorescence according to claim 11, wherein the tube path through which the optical fiber is run is led through an inner area of a treating instrument of the endoscope.

13. The apparatus of claim 10, further comprising a stimulating light source providing the stimulating light, wherein the stimulating light source outputs a constant stimulating light for the mucosa and sub mucosa.

14. An apparatus for detecting fluorescence comprising:

an optical system guiding light emitted from an organic tissue; and distinguishing means receiving light from the optical system for making judgment on whether or not a sub mucosa and a mucosa coexist on an area under examination based on autofluorescence emitted from the organic tissue within the area under examination in response to stimulating light projected thereon, wherein the distinguishing means makes judgment by comparing the normalized intensity of the autofluorescence emitted from the organic tissue with a standard value which is decided based on at least one of: the normalized intensity of autofluorescence emitted from the sub mucosa and the normalized intensity of autofluorescence emitted from the mucosa, wherein the autofluorescence emitted from the organic tissue has an overall interated intensity, said apparatus further comprising means for filtering the autofluorescence emitted from the organic tissue to isolate a first wavelength region, and wherein the normalized intensity comprises the intensity of the autofluorescence in the first wavelength region, divided by the intensity over the overall integrated intensity.

15. An apparatus for detecting fluorescence according to claim 14, said apparatus being operable with an endoscope further comprising:

an optical fiber for transferring the autofluorescence emitted from the organic tissue which is incident on one end thereof to the distinguishing means, wherein
the optical fiber is run through a tube path extending between a handling portion and the operating end of the endoscope.

16. An apparatus for detecting fluorescence according to claim 15, wherein the tube path through which the optical fiber is run is led through an inner area of a treating instrument of the endoscope.

17. An apparatus for detecting fluorescence according to any of claims 6–16, wherein each of said normalized intensities is the normalized band intensity for a wavelength region near 480 nm.

* * * * *